(12) United States Patent
Esmond et al.

(10) Patent No.: US 7,300,927 B2
(45) Date of Patent: Nov. 27, 2007

(54) METHOD FOR TREATING OR PREVENTING ALZHEIMER'S DISEASE

(75) Inventors: Robert W. Esmond, 312 Blair Ct., NW., Vienna, VA (US) 22180; Jack R. Wands, 210 Varick Rd., Waban, MA (US) 02168; Suzanne de la Monte, 1040 High Hawk Rd., East Greenwich, RI (US) 02818

(73) Assignees: Robert W. Esmond, Vienna, VA (US); Jack R. Wands, Waban, MA (US); Suzanne de la Monte, East Greenwich, RI (US)

( * ) Notice: Subject to any disclaimer, the term of this patent is extended or adjusted under 35 U.S.C. 154(b) by 0 days.

(21) Appl. No.: 10/669,217

(22) Filed: Sep. 23, 2003

(65) Prior Publication Data

US 2004/0060077 A1 Mar. 25, 2004

Related U.S. Application Data

(63) Continuation of application No. 09/394,712, filed on Sep. 13, 1999, which is a continuation of application No. PCT/US98/04731, filed on Mar. 12, 1998.

(60) Provisional application No. 60/039,607, filed on Mar. 12, 1997.

(51) Int. Cl.
*A61K 31/555* (2006.01)
*A61K 31/415* (2006.01)

(52) U.S. Cl. ............... 514/188; 514/186; 514/387

(58) Field of Classification Search ............ 514/655, 514/369, 188; 424/23
See application file for complete search history.

(56) References Cited

U.S. PATENT DOCUMENTS

| | | | |
|---|---|---|---|
| 4,287,200 A | 9/1981 | Kawamatsu et al. |
| 4,340,605 A | 7/1982 | Kawamatsu et al. |
| 4,376,777 A | 3/1983 | Kawamatsu et al. |
| 4,438,141 A | 3/1984 | Kawamatsu et al. |
| 4,444,779 A | 4/1984 | Kawamatsu et al. |
| 4,461,902 A | 7/1984 | Kawamatsu et al. |
| 4,540,564 A | 9/1985 | Bodor |
| 4,546,095 A | 10/1985 | Markov |
| 4,572,912 A | 2/1986 | Yoshioka et al. |
| 4,683,195 A | 7/1987 | Mullis et al. |
| 4,683,202 A | 7/1987 | Mullis |
| 4,687,777 A | 8/1987 | Meguro et al. |
| 4,703,040 A | 10/1987 | Markov |
| 4,703,052 A | 10/1987 | Eggler et al. |
| 4,725,610 A | 2/1988 | Meguro et al. |
| 4,757,052 A | 7/1988 | Markov |
| 4,775,665 A | 10/1988 | Wurtman |
| 4,855,306 A | 8/1989 | Markstein et al. |
| 4,873,191 A | 10/1989 | Wagner et al. |
| 4,873,255 A | 10/1989 | Yoshioka et al. |
| 4,897,393 A | 1/1990 | Iijima et al. |
| 4,897,405 A | 1/1990 | Alessi et al. |
| 4,918,091 A | 4/1990 | Cantello et al. |
| 4,948,900 A | 8/1990 | Iijima et al. |
| 4,965,188 A | 10/1990 | Mullis et al. |
| 4,980,350 A | 12/1990 | MacCoss |
| 5,002,953 A | 3/1991 | Hindley |
| 5,039,665 A | 8/1991 | Markov |
| 5,039,794 A | 8/1991 | Wier et al. |
| 5,061,717 A | 10/1991 | Clark et al. |
| 5,120,754 A | 6/1992 | Clark et al. |
| 5,132,317 A | 7/1992 | Cantello et al. |
| 5,143,929 A | 9/1992 | Belliotti et al. |
| 5,164,384 A | 11/1992 | Paul |
| 5,194,443 A | 3/1993 | Hindley |
| 5,208,250 A | 5/1993 | Cetenko et al. |
| 5,223,522 A | 6/1993 | Clark et al. |
| 5,232,925 A | 8/1993 | Hindley et al. |
| 5,260,445 A | 11/1993 | Hindley |
| 5,270,319 A | 12/1993 | Belliotti et al. |
| 5,283,260 A | 2/1994 | Miller |
| 5,326,770 A | 7/1994 | Wilkerson |
| 5,364,769 A | 11/1994 | Rosenthal |
| 5,395,822 A | 3/1995 | Izumi et al. |
| 5,457,109 A | 10/1995 | Antonucci et al. |
| 5,463,070 A | 10/1995 | Goldstein |
| 5,468,755 A | 11/1995 | Cincotta |

(Continued)

FOREIGN PATENT DOCUMENTS

EP 0 587 377 A2 3/1994

(Continued)

OTHER PUBLICATIONS

Antonucci et al., "Impaired Glucose Tolerance is Normalized by Treatment With the Thiazolidinedione Troglitazone," Diabetes Care 20:188-193 (1997).

(Continued)

*Primary Examiner*—Michael G. Hartley
*Assistant Examiner*—Jagadishwar Samala
(74) *Attorney, Agent, or Firm*—Finnegan, Henderson, Farabow, Garrett & Dunner, LLP

(57) ABSTRACT

Disclosed is a method for treating or preventing Alzheimer's disease by restricting the level of metabolizable carbohydrate in the diet and/or administering to the patient an effective amount of an agent which reduces serum insulin levels.

5 Claims, No Drawings

U.S. PATENT DOCUMENTS

| | | | |
|---|---|---|---|
| 5,472,980 | A | 12/1995 | Miller |
| 5,478,852 | A | 12/1995 | Olefsky et al. |
| 5,494,927 | A | 2/1996 | Cetenko et al. |
| 5,523,314 | A | 6/1996 | Bue-Valleskey et al. |
| 5,534,615 | A | 7/1996 | Baker et al. |
| 5,543,297 | A | 8/1996 | Cromlish et al. |
| 5,545,410 | A | 8/1996 | Fox et al. |
| 5,556,843 | A | 9/1996 | Romeo et al. |
| 5,594,015 | A | 1/1997 | Kurtz et al. |
| 5,597,832 | A | 1/1997 | Michaelides et al. |
| 5,602,120 | A | 2/1997 | Fu et al. |
| 5,602,121 | A | 2/1997 | Fu |
| 5,607,967 | A | 3/1997 | Friedman et al. |
| 5,612,312 | A | 3/1997 | Moses et al. |
| 5,614,541 | A | 3/1997 | Bäckström et al. |
| 5,618,835 | A | 4/1997 | Wu et al. |
| 5,641,796 | A | 6/1997 | Dominianni et al. |
| 5,646,168 | A | 7/1997 | Goldstein |
| 5,668,117 | A * | 9/1997 | Shapiro ............... 514/55 |
| 5,700,820 | A | 12/1997 | Vyas et al. |
| 5,707,971 | A | 1/1998 | Fahy |
| 5,714,470 | A | 2/1998 | Peet et al. |
| 5,716,975 | A | 2/1998 | Bue-Valleskey |
| 5,783,556 | A | 7/1998 | Clark et al. |
| 5,789,401 | A * | 8/1998 | McCarty ............... 514/188 |
| 5,814,647 | A | 9/1998 | Urban et al. |
| 5,824,692 | A | 10/1998 | Lippiello et al. |
| 5,925,657 | A | 7/1999 | Seed et al. |
| 5,935,927 | A | 8/1999 | Vitek et al. |
| 6,025,157 | A | 2/2000 | Klein et al. |
| 6,028,088 | A | 2/2000 | Pershadsingh et al. |
| 6,087,384 | A | 7/2000 | Matsui et al. |
| 6,117,911 | A | 9/2000 | Grainger et al. |
| 6,191,154 | B1 | 2/2001 | Landreth et al. |
| 6,399,639 | B1 | 6/2002 | Matsui et al. |
| 6,555,565 | B2 | 4/2003 | Matsui et al. |
| 6,746,678 | B1 * | 6/2004 | Shapiro ............... 424/400 |

FOREIGN PATENT DOCUMENTS

| | | |
|---|---|---|
| EP | 0 587 377 A3 | 3/1994 |
| EP | 0 677 517 A1 | 10/1995 |
| JP | 07-238035 A2 | 9/1995 |
| WO | WO89/08651 | 9/1989 |
| WO | WO90/08832 | 8/1990 |
| WO | WO91/07107 | 5/1991 |
| WO | WO92/02520 | 2/1992 |
| WO | WO93/24115 | 12/1993 |
| WO | WO94/04133 | 3/1994 |
| WO | WO94/23756 | 10/1994 |
| WO | WO95/13823 | 5/1995 |
| WO | WO96/03087 | 2/1996 |
| WO | WO96/15272 | 5/1996 |
| WO | WO96/33724 | 10/1996 |
| WO | WO97/31907 | 9/1997 |
| WO | WO98/29411 | 7/1998 |
| WO | WO98/29415 | 7/1998 |
| WO | WO98/39006 | 9/1998 |
| WO | WO98/40386 | 9/1998 |
| WO | WO98/41201 | 9/1998 |
| WO | WO99/16758 | 4/1999 |
| WO | WO99/20614 | 4/1999 |
| WO | WO99/38850 | 8/1999 |
| WO | WO99/46268 | 9/1999 |
| WO | WO 00/23407 | 4/2000 |
| WO | WO 00/23415 | 4/2000 |
| WO | WO 00/23416 | 4/2000 |
| WO | WO 00/23417 | 4/2000 |
| WO | WO 00/23445 | 4/2000 |
| WO | WO 00/23451 | 4/2000 |
| WO | WO 00/32190 | 6/2000 |
| WO | WO 00/35437 | 6/2000 |

OTHER PUBLICATIONS

Atkins, Robert C. M.D. and Atkins, Veronica., *Dr. Atkins' Quick & Easy New Diet Cookbook*, Fireside, New York, NY, © 1997.

Balentine, "Pathology of Experimental Spinal Cord Trauma I. The Necrotic Lesion as a Function of Vascular Injury," Lab. Invest. 39:236-253 (1978).

Banati et al., "Cytotoxicity of Microglia," Glia 7.111-118 (1993).

Basso et al., "Graded Histological and Locomotor Outcomes after Spinal Cord Contusion Using the NYU Weight-Drop Device versus Transection," Exp. Neurol. 139:244-256 (1996).

Bauer et al., "Expression and Regulation of Cyclooxygenase-2 in Rat Microglia," Eur. J. Biochem. 243:726-731 (1997).

Beaudet, "Bibliography of Cloned Human and Other Selected DNAs," Am. J. Hum. Genet. 37:386-406 (1985).

Berge et al., "Pharmaceutical Salts," J. Pharm. Sciences 66:1-19 (1977).

Bernstein, H.G. et al., "Insulin-degrading enzyme in the Alzheimer's disease brain: prominent localization in neurons and senile plaques," Neurosci. Lett. 263:161-4 (1999).

Berton and Gordon, "Modulation of Macrophage Mannosyl-Specific Receptors by Cultivation on Immobilized Zymosan, Effects on Superoxide-Anion Release and Phagocytosis," Immunology 49:705-715 (1983).

Blight, "Effects of Silica on the Outcome From Experimental Spinal Cord Injury: Implication of Macrophages in Secondary Tissue Damage," Neuroscience 60:263-273 (1994).

Blum-Degan, D. et al. "Altered regulation of brain glucose metabolism as a cause of neurodegenerative disorders?," J. Neural Transm. Suppl. 46:139-47 (1995).

Borchelt et al., "Accelerated Amyloid Deposition in the Brains of Transgenic Mice Coexpressing Mutant Presenilin 1 and Amyloid Precursor Proteins," Neuron 19:939-945 (1997).

Boshart et al., "A Very Strong Enhancer is Located Upstream of an Immediate Early Gene of Human Cytomegalovirus," Cell 41:521-530 (1985).

Bradford, "A Rapid and Sensitive Method for the Quantitation of Microgram Quantities of Protein Utilizing the Principle of Protein-Dye Binding," Anal. Biochem. 72:248-254 (1976).

Bradley et al., "Formation of Germ-Line Chimaeras From Embryo-Derived Teratocarcinoma Cell Lines," Nature 309:255-258 (1984).

Brennan, M.B., "Bringing Back the Memories. Expanding understanding of Alzheimer's disease drives development of new drugs," Chem. Eng. News, pp. 29-32 and 34-35 (Jan. 20, 1997).

Brinster et al., "Factors Affecting the Efficiency of Introducing Foreign DNA into Mice by Microinjecting Eggs," Proc. Natl. Acad. Sci. USA 82:4438-4442 (1985).

Brown et al., "Role of Microglia and Host Prion Protein in Neurotoxicity of a Prion Protein Fragment," Nature 380:345-347 (1996).

Burridge and Chrzanowska-Wodnicka, "Focal Adhesions, Contractility, and Signaling," Annu. Rev. Cell Dev. Biol. 12:463-519 (1996).

Camras et al., "Latanoprost, a Prostaglandin Analog, for Glaucoma Therapy, Efficacy and Safety after 1 Year of Treatment in 198 Patients," Ophthalmology 103:1916-1924 (1996).

Chamberlin et al., "New RNA Polymerase from *Escherichia coli* Infected with Bacteriophage T7," Nature 228:227-231 (1970).

Christensen, J. "Low-Fat Diet, Dementia Linked," Associated Press article accessed on compuserve.com (Jul. 28, 1999).

Combs, C.K. et al., "Inflamatory Mechanisms in Alzheimer's Disease: Inhibition of β-Amyloid Stimulated Proinflammatory Responses and Neurotoxicity by PPARγ Agonists," J. Neurosci. 20:558-567 (2000).

Constantini and Young, "The Effects of Methylprednisolone and the Ganglioside GM1 on Acute Spinal Cord Injury in Rats," J. Neurosurg. 80:97-111 (1994).

Cotman et al., "β-Amyloid Converts an Acute Phase Injury Response to Chronic Injury Responses," Neurobiol. Aging 17:723-731 (1996).

Craft, S. et al., "Effects of Hyperglycemia on Memory and Hormone Levels in Dementia of the Alzheimer Type: A Longitudinal Study," Behav. Biosci. 107:926-940 (1993).

Craft, S. et al., "Memory improvement following induced hyperinsulinemia in Alzheimer's disease," Neurobiol. Aging 17:123-30 (1996).

Craft, S. et al. "Enhancement of memory in Alzheimer disease with insulin and somatostatin, but not glucose," Arch. Gen. Psychiatry 56:1135-40 (1999).

Craft, S. et al., "Cerebrospinal fluid and plasma insulin levels in Alzheimer's disease: relationship to severity of dementia and apolipoprotein E genotype," Neurology 50:164-8 (Jan. 1998).

Curb, J.D. et al. "Longitudinal association of vascular and Alzheimer's dementias, diabetes, and glucose tolerance," Neurology 52:971-975 (1999).

Czop, "Phagocytosis of Particulate Activators of the Alternative Complement Pathway: Effects of Fibronectin," Adv. Immunol. 38:361-398 (1986).

Daum and Rohrbach, "Zymosan Induces Selective Release of Arachidonic Acid From Rabbit Alveolar Macrophages Via Stimulation of a β-Glucan Receptor," FEBS 309:119-122 (1992).

Dijkema et al., "Cloning and Expression of the Chromosomal Immune Interferon Gene of the Rat," EMBO J. 4:761-767 (1985).

Ducker et al., "Pathological Findings in Acute Experimental Spinal Cord Trauma," J. Neurosurg. 35:700-708 (1971).

Duelli et al., "Intracerebroventricular Injection of Streptozotocin Induces Discrete Local Changes in Cerebral Glucose Utilization in Rats," Int. J. Devl. Neuroscience 12:737-743 (1994).

Eades and Eades, "Protein Power," pp. 30-71, 114-123 and 166-167, Bantam Books, New York, NY (1996).

Erlich (ed.), PCR Technology, Stockton Press, New York (1989).

Evans et al., "Establishment in Culture of Pluripotential Cells From Mouse Embryos," Nature 292:154-156 (1981).

Fitch and Silver, "Activated Macrophages and the Blood-Brain Barrier: Inflammation after CNS Injury Leads to Increases in Putative Inhibitory Molecules," Exp. Neuro. 148:587-603 (1997).

Fitch et al., "Cellular and Molecular Mechanisms of Glial Scarring and Progressive Cavitation: In Vivo and In Vitro Analysis of Inflammation-Induced Secondary Injury after CNS Trauma," J. Neurosci. 19:8182-8198 (1999).

Foster, D.W., "Diabetes Mellitus," Harrison's Principals of Internal Medicine, 11th Ed., pp. 1778-1797 (1987).

Franzese et al., "Effect of Prostaglandin $A_1$ on Proliferation and Telomerase Activity of Human Melanoma Cells In Vitro," Melanoma Res. 8:323-328 (1998).

Frautschy et al., "Microglial Response to Amyloid Plaques in APPsw Transgenic Mice," Am. J. Pathol. 152:307-317 (1998).

Frolich, L. et al., "Brian insulin and insulin receptors in aging and sporadic Alzheimer's disease," J. Neural Transm. 105:423-38 (1998).

Fukumoto et al., "Association of !340-positive Senile Plaques with Microglial Cells in the Brains of Patients with Alzheimer's Disease and in Non-demented Aged Individuals," Neurodgen. 5:13-17 (1996).

Gambassi, G. and Bernabei, R., "Insulin, diabetes mellitus, Alzheimer's disease and apolipoprotein E," Neurology 51:925-6 (Sep. 1998).

Gaupp et al., "Modulation of Experimental Autoimmune Neuritis in Lewis Rats by Oral Application of Myelin Antigens," J. Neuroimmunol. 79:129-137 (1997).

Ghazizadeh et al., "Physical and Functional Association of Src-related Protein Tyrosine Kinases with FcγRII in Monocytic THP-1 Cells," J. Biol. Chem. 269:8878-8884 (1994).

Ghazzi et al., "Cardiac and Glycemic Benefits of Troglitazone Treatment in NIDDM," Diabetes 46:433-439 (1997).

Giulian et al., "Phagocytic Microglia Release Cytokines and Cytotoxins that Regulate the Survival of Astrocytes and Neurons in Culture," Neurochem. Int. 25:227-233 (1994).

Giulian et al., "Senile Plaques Stimulate Microglia to Release a Neurotoxin Found in Alzheimer Brain," Neurochem. Int. 27:119-137 (1995).

Giulian, "Reactive Glia as Rivals in Regulating Neuronal Survival," Glia 7:102-110 (1993).

Giulian et al., "The Role of Mononuclear Phagocytes in Wound Healing After Traumatic Injury to Adult Mammalian Brain," J. Neurosci. 9:4416-4429 (1989).

Giulian et al., "Specific Domains of Ǝ-Amyloid from Alzheimer Plaque Elicit Neuron Killing in Human Microglia," J. Neurosci. 16:6021-6037 (1996).

Giulian et al., "The Impact of Microglia-Derived Cytokines upon Gliosis in the CNS," Dev. Neurosci. 6:128-136 (1994).

Giulian and Lachman, "Interleukin-1 Stimulation of Astroglial Proliferation After Brain Injury," Science 228:497-499 (1985).

Gorman et al., "The Rous Sarcoma Virus Long Terminal Repeat is a Strong Promoter When Introduced into a Variety of Eukaryotic Cells by DNA-Mediated Transfection," Proc. Natl. Acad. Sci. USA 79:6777-6781 (1982).

Gossler et al., "Transgenesis by Means of Blastocyst-Derived Embryonic Stem Cell Lines," Proc. Natl. Acad. Sci. USA 83:9065-9069 (1986).

Graham and Van Der Eb, "A New Technique for the Assay of Infectivity of Human Adenovirus 5 DNA," Virol. 52:456-467 (1973).

Granneman et al., "Member of the Peroxisome Proliferator—Activated Receptor Family of Transcription Factors Is Differentially Expressed by Oligodendrocytes," J. Neurosci. Res. 51:563-573 (1998).

Guth et al., "Essentiality of a Specific Cellular Terrain for Growth of Axons into a Spinal Cord Lesion," Exp. Neurol. 88:1-12 (1985).

Guth et al., "Key Role for Pregnenolone in Combination Therapy that Promotes Recovery after Spinal Cord Injury," Proc. Natl. Acad. Sci. USA 91:12308-12312 (1994).

Guth et al., "Spinal Cord Injury in the Rat: Treatment with Bacterial Lipopolysaccharide and Indomethacin Enhances Cellular Repair and Locomotor Function," Exp. Neurol. 126:76-87 (1994).

Hashimoto et al., "Nitric Oxide Synthesis in Murine Peritoneal Macrophages by Fungal Ǝ-Glucans," Biol. Pharm. Bull. 20:1006-1009 (1997).

Haskell and Bowen, "Efficient Production of Transgenic Cattle by Retroviral Infection of Early Embryos," Mol. Reprod. Dev., 40:386-390 (1995).

Heitner, J. and Dickson, D., Diabetics do not have increased Alzheimer-type pathology compared with age-matched control subjects. A retrospective postmortem immunocytochemical and histoflourescent study, Neurology 49:1306-11 (Nov. 1997).

Heun et al., "The Validity of Psychometric Instruments for Detection of Dementia in the Elderly General Population," Int. J. Geriatr. Psychiatry 13:368-380 (1998).

Hillhouse et al., "Middle Cerebral Artery Occlusion in the Rat Causes a Biphasic Production of Immunoreactive Interleukin-1Ǝ in the Cerebral Cortex," Neurosci. Lett. 249:177-179 (1998).

Ho et al., "Human Autoimmune Neuropathies," Annu. Rev. Neurosci. 21:187-226 (1998).

Hogan et al., Manipulating the Mouse Embryo, Cold Spring Harbor Laboratory Press, Cold Spring Harbor, N.Y. (1986).

Holden, R.J., and Mooney, P.A., "Interleukin-1β: a common cause of Alzheimer's Disease and Diabetes Mellitus," Med. Hypothesis 45:559-71 (1995).

Hoyer, S., et al., "Desensitization of brain insulin receptor. Effect on glucose/energy and related metabolism," J. Neural Transm. Suppl. 44:259-68 (1994).

Hoyer et al., "Brain Glucose Metabolism Is Controlled by Amplification and Desensitization of the Neuronal Insulin Receptor," Annals of the NY Academy of Sciences 777:374-379 (1996).

Hoyer, S., "Oxidative metabolism deficiencies in brains of patients with Alzheimer's disease," Acta Neurol. Scand. Suppl. 165:18-24 (1996).

Hoyer, S., "Models of Alzheimer's disease: cellular and molecular aspects," J. Neural. Transm. Suppl. 49:11-21 (1997).

Hoyer, S., "Is sporadic Alzheimer disease of the brain type of non-insulin dependent diabetes mellitus? A challenging hypothesis," J. Neural Transm. 105:415-22 (1998).

Hulin B. et al., "Novel Thiazolidine-2,4-diones as Potent Euglycemic Agents," J. Med. Chem. 35: 1853-1864 (1992).

Hwang et al., "Expression of Mitogen-Inducible Cyclooxygenase Induced by Lipopolysaccharide: Mediation Through Both Mitogen- Activated Protein Kinase and NF-KB Signaling Pathways in Macrophages," Biochem. Pharmacol. 54:87-96 (1997).

Ii et al., "β-Amyloid Protein-Dependent Nitric Oxide Production From Microglial Cells and Neurotoxicity," Brain Res. 720:93-100 (1996).

Inoue et al., "Transcriptional Regulation of Human Prostaglandin-endoperoxide Synthase-2 Gene by Lipopolysaccharide and Phorbol Ester in Vascular Endothelial Cells," J. Biol. Chem. 270:24965-24971 (1995).

Itagaki et al., "Relationship of Microglia and Astrocytes to Amyloid Deposits of Alzheimer Disease," J. Neuroimmunol. 24:173-182 (1989).

Iwamoto et al., "Effect of New Oral Antidiabetic Agent CS-045 on Glucose Tolerance and Insulin Secretion in Patients with NIDDM," Diabetes Care 14:1083-1086 (1991).

Iwamoto et al., "Effects of Troglitazone: A New Hypoglycemic Agent in Patients with NIDDM Poorly Controlled by Diet Therapy," Diabetes Care 19:151-156 (1996).

Jaenisch, "Germ Line Integration and Mendelian Transmission of the Exogenous Moloney Leukemia Virus," Proc. Nat. Acad. Sci. USA 73:1260-1264 (1976).

Jaenisch, "Transgenic Animals," Science 240:1468-1474 (1988).

Jähner et al., "Insertion of the Bacterial $GPT$ Gene into the Germ Line of Mice by Retroviral Infection," Proc. Natl. Acad. Sci. USA 82:6927-6931 (1985).

Jähner et al., "$De\ Novo$ Methylation and Expression of Retroviral Genomes During Mouse Embryogenesis," Nature 298:623-628 (1982).

Jiang et al., "PPAR-γ Agonists Inhibit Production of Monocyte Inflammatory Cytokines," Nature 39:82-86 (1998).

Johnson et al., "Troglitazone: Review and Assessment of Its Role in the Treatment of Patients with Impaired Glucose Tolerance and Diabetes Mellitus," Ann. Pharma. 32:337-348 (1998).

Kacian et al., "A Replicating RNA Molecule Suitable for a Detailed Analysis of Extracellular Evolution and Replication," Proc. Nat. Acad. Sci. USA 69:3038-3042 (1972).

Kao et al., "The Mechanism of Spinal Cord Cavitation Following Spinal Cord transection," J. Neurosurg. 46:757-766 (1977).

Kaufmann et al., "Cyclooxygenases and the Central Nervous System," Prostaglandins 54:601-624 (1997).

Kiener et al., "Cross-linking of FcY Receptor I (FcYRI) and Receptor II (FcYRII) on Monocytic Cells Activates a Signal Transduction Pathway Common to Both Fc Receptors That Involves the Stimulation of p72 Syk Protein Tyrosine Kinase," J. Biol. Chem. 268:24442-24448 (1993).

Kilander, L. et al., "Peripheral glucose metabolism and insulin sensitivity in Alzheimer's disease," Acta Neurol. Scand. 87:294-298 (1993).

Kim et al., "Use of the Human Elongation Factor 1∀ Promoter as a Versatile and Efficient Expression System," Gene 91:217-223 (1990).

Kitamura et al., "Increased Expression of Cyclooxygenases and Peroxisome Proliferator-Activated Receptor-γ in Alzheimer's Disease Brains," Biochem. and Biophysical Res. Comms. 254:582-586 (1999).

Kretzschmar et al., "Cell Death in Prion Disease," J. Neural Transm. 50:191-210 (1997).

Kuusisto, J. et al, "Association between features of the insulin resistance syndrome and Alzheimer's disease independently of the apolipoprotein E4 phenotype: cross sectional population based study," BMJ 315:1045-9 (Oct. 1997).

Laedtke, T.W. et al., "Are Alzheimer's Disease (AD) and Non-Insulin-Dependent Diabetes Mellitus (NIDDM) Related?", $Clinical\ Research$, 42(1):65A, 1994.

Lagenaur and Lemmon, "An L1-Like Molecule, the 8D9 Antigen, is a Potent Substrate for Neurite Extension," Proc. Natl. Acad. Sci. USA 84:7753-7757 (1987).

Lemberger et al., "Peroxisome Proliferator-Activated Receptors: A Nuclear Receptor Signaling Pathway in Lipid Physiology," Annu. Rev. Cell Dev. Biol. 12:335-363 (1996).

Lev et al., "Protein Tyrosine Kinase PYK2 Involved in $Ca^{2+}$-Induced Regulation of Ion Channel and MAP Kinase Functions," Nature 376:737-745 (1995).

Lithner, F., "Diabetes and Alzheimer's disease," Diabetologia 39:1242 (1996).

Loi et al., "Meta-Analysis of Steady-State Pharmacokinetics of Troglitazone and Its Metabolites," J. Clin. Pharmacol. 37:1038-1047 (1997).

Lombard et al., "A New Method for Studying the Binding and Ingestion of Zymosan Particles of Macrophages," J. Immunol. Methods 174:155-165 (1994).

Maniatis et al., Molecular Cloning, A Laboratory Manual, Cold Spring Harbor Laboratory Press, New York (1982).

Maniatis et al., "Regulation of Inducible and Tissue-Specific Gene Expression," Science 236:1237-1245 (1987).

Mann et al, "Microglial Cells and Amyloid β Protein (Aβ) Deposition: Association with $Aβ_{40}$-Containing Plaques," Acta Neuropathol 90:472-477 (1995).

Martiney et al., "Prevention and Treatment of Experimental Autoimmune Encephalomyelitis by CN1-1493, a Macrophage-Deactivating Agent," J. Immunol. 160:5588-5595 (1998).

Masliah et al., "Comparison of Neurodegenerative Pathology in Transgenic Mice Overexpressing V717F β-Amyloid Precursor Protein and Alzheimer's Disease," J. Neurosci. 16:5795-5811 (1996).

McDonald et al., "β-Amyloid Fibrils Activate Parallel Mitogen-Activated Protein Kinase Pathways in Microglia and THP1 Monocytes," J. Neurosci. 18:4451-4460 (1998).

McDonald et al., "Amyloid Fibrils Activate Tyrosine Kinase-Dependent Signaling and Superoxide Production in Microglia," J. Neurosci. 17:2284-2294 (1997).

McGeer and Rogers, "Anti-inflammatory Agents as a Therapeutic Approach to Alzheimer's Disease," Neurology 42:447-449 (1992).

Means and Anderson, "Neuronophagia by Leukocytes in Experimental Spinal Cord Injury," J. Neuropath. Exp. Neurol. 42:707-719 (1983).

Miyazono et al., "A Comparative Immunohistochemical Study of Kuru and Senile Plaques with a Special Reference to Glial Reactions at Various Stages of Amyloid Plaque Formation," Am. J. Path. 139:589-598 (1991).

Mizushima and Nagata, "pEF-BOS, a Powerful Mammalian Expression Vector," Nuc. Acids Res. 18:5322 (1990).

Mukherjee et al., "Sensitization of Diabetic and Obese Mice to Insulin by Retinoid X Receptor Agonists," Nature 386:407-410 (1997).

Nelson et al., "The Effect of Dietary Docosahexaenoic Acid of Plasma Lipoproteins and Tissue Fatty Acid Composition in Humans," Lipids 32:1137-1146 (1997).

Nolan et al., "Improvement in Glucosse Tolerance and Insulin Resistance in Obese Subjects Treated with Troglitazone," N. Engl. J. Med. 331:1188-1193 (1994).

Oakes et al., "The Insulin Sensitizer, BRL 49653, Reduces Systemic Fatty Acid Supply and Utilization and Tissue Lipid Availability in the Rat," Metabolism 46:935-942 (1997).

O'Brien, J.T. et al., "The Function of the Hypothalmic-Pituitary-Adrenal Axis in Alzheimer's Disease. Response to Insulin Hypoglycemia," Brit. J. Psych. 165:650-657 (1994).

Ogihara et al., "Enhancement of Insulin Sensitivity by Troglitazone Lowers Blood Pressure in Diabetic Hypertensives," Am. J. Hypertens. 8:316-320 (1995).

Ofek et al., "Nonopsonic Phagocytosis of Microorganisms," Annu. Rev. Microbiol. 49:239-276 (1995).

Ott, A. et al., "Diabetes mellitus and the risk of dementia: The Rotterdam Study," Neurology 53:1937-42 (1999).

Perlmutter et al., "Morphologic Association Between Microglia and Senile Plaque Amyloid in Alzheimer's Disease," Neurosci. Lett. 119:32-36 (1990).

$Physicians'\ Desk\ Reference$, Medical Economics Company, Montvale, NJ, 595-597 and 2118-2121, © 1998.

$Physicians'\ Desk\ Reference$, Medical Economics Company, Montvale, NJ, 2278-2282 and 3088-3092, © 2000.

Razay, G., and Wilcock, G.K., "Hyperinsulinaemia and Alzheimer's Desease," Age and Aging 23:396-399 (1994).

Remington's Pharmaceutical Sciences, A.R. Gennaro, ed., Mack Publishing Co., PA (1990).

Reuters Medical News for the Professional, "Estrogen Replacement Therapy Does Not Reduce Alzheimer's Risk," Reuters Ltd. (2001)

accessed on Apr. 3, 2001, at http://neurology.medscape.com/reuters/prof/2001/03/03.27/20010326epid001.html.

Rich et al., "Nonsteroidal Anti-inflammatory Drugs in Alzheimer's Disease," Neurology 45:51-55 (1995).

Ricote et al., "The Peroxisome Proliferator-Activated Receptor-Y is a Negative Regulator of Macrophage Activation," Nature 391:79-82 (1998).

Robertson et al., Germ-line Transmission of Genes Introduced into Cultured Pluripotential Cells by Retroviral Vector, Nature 323:445-448 (1986).

Rogers et al., "Donepezil Improves Cognition and Global Function in Alzheimer Disease," Arch Intern. Med. 158:1021-1031 (1998).

Rogers et al., "Inflammation and Alzheimer's Disease Pathogenesis," Neurobiol Aging 17:681-686 (1996).

Rothwell et al., The Role of Interleukin 1 in Acute Neurodegeneration and Stroke: Pathophysiological and Therapeutic Implications, J. Clin. Invest. 100:2648-2652 (1997).

Saltiel and Olefsky, "Thiazolidinediones in the Treatment of Insulin Resistance and Type II Diabetes," Diabetes 45:1661-1669 (1996).

Sambrook et al., Molecular Cloning: A Laboratory Manual, 2nd Ed., Cold Spring Harbor Laboratory Press, New York 6.9-6.15; 16.7-16.8 (1989).

Sano et al., "A Controlled Trial of Selegiline, Alpha-Tocopherol, or Both as Treatment of Alzheimer's Disease," New Engl. J. Med. 336:1216-1222 (1997).

Scammell et al., "Activation of Ventrolateral Preoptic Neurons by the Somnogen Prostaglandin $D_2$," Proc. Nat. Acad. Sci. 95:7754-7759 (1998).

Schoenle, E.J. et al., "Recombinant human insulin-like growth factor I (rhIGF I) reduces hyperglycaemia in patients with extreme insulin resistance," *Diabetologia*, 34:675-679, 1991.

Sharma and Kumar,"Role of Proinflammatory Cytokines in Cerebral Ischemia: A Review," Met. Brain Dis. 13:1-8 (1998).

Smith et al., "Prostaglandin Endoperoxide H Synthases (Cyclooxygenases)-1 and -2," J. Biol. Chem. 271:33157-33160 (1996).

Stewart et al., "Expression of Retroviral Vectors in Transgenic Mice Obtained by Embryo Infection," EMBO J. 6:383-388 (1987).

Stewart et al., "Risk of Alzheimer's Disease and Duration of NSAID Use," Neurology 48:626-632 (1997).

Stewart and Weir, "Carbohydrates as Recognition Molecules in Macrophage Activities," J. Clin. Lab. Immunol. 28:103-108 (1989).

Sturchler-Pierrat et al., "Two Amyloid Precursor Protein Transgenic Mouse Models with Alzheimer Disease-Like Pathology," Proc. Natl. Acad. Sci. USA 94:13287-13292 (1997).

Suter et al., "Metabolic Effects of New Oral Hypoglycemic Agent CS-045 in NIDDM Subjects," Diabetes Care 15:193-203 (1992).

Szczepanik et al., "Effects of Chronic Intrahippocampal Infusion of Lipopolysaccharide in the Rat," Neuroscience 70:57-65 (1996).

Tapper and Sundler, "Glucan Receptor and Zymosan-Induced Lysosomal Enzyme Secretion in Macrophages," Biochem. J. 306:829-835 (1995).

Tsai and Wiltbank, "Prostaglandin $F_{2\gamma}$ Induces Expression of Prostaglandin G/H Synthase-2 in the Ovine Corpus Luteum: A Potential Positive Feedback Loop during Luteolysis," Biol. Reprod. 57:1016-1022 (1997).

Tsuchiya et al., "Induction of Maturation in Cultured Human Monocytic Leukemia Cells by a Phorbol Diester," Cancer Res. 42:1530-1536 (1982).

Urbanics, R., "Alzheimer's: IBC's Ninth Annual Conference, Gene Discovery to Therapeutic Applications," IDdb Meeting Report, Current Drugs, Ltd (2001), accessed on Mar. 15, 2001, at http://www.iddb3.com/iddb3/report_reference.display-reference?i_reference_id=400407.

Uetsuki et al., "Isolation and Characterization of the Human Chromosomal Gene for Polypeptide Chain Elongation Factor-$1\alpha$," J. Biol. Chem. 264:5791-5798 (1989).

Usala, Anton-Lewis M.D. et al., "Brief Report: Treatment of Insulin-Resistant Diabetic Ketoacidosis with Insulin-like Growth Factor I in an Adolescent with Insulin-Dependent Diabetes," *The New England Journal of Medicine*, 327(12):853-857, 1992.

Van Der Putten et al., "Efficient Insertion of Genes into the Mouse Germ Line Via Retroviral Vectors," Proc. Natl. Acad. Sci. USA 82:6148-6152 (1985).

Vane et al., "Cyclooxygenases 1 and 2," Annu. Rev. Pharm. Tox. 38:97-120 (1998).

Vanhanen, M. and Soininen, H., "Glucose intolerance, cognitive impairment and Alzheimer's disease," Curr. Opin. Neurol. 11:673-7 (Dec. 1998).

Voss et al., "The Role of Enhancers in the Regulation of Cell-Type-Specific Transcriptional Control," Trends Biochem. Sci. 11:287-289 (1986).

Waldron, T., "Insulin Resistance a Potential Etiologic Link to Alzheimer's," Medical Tribune: Internist & Cardiologist Edition. 39(8): (1998), accessed on Medscape web site on Jan. 31, 2000.

Wallace et al., "Chronic Regenerative Changes in the Spinal Cord after Cord Compression Injury in Rats," Surg. Neurol. 27:209-219 (1987).

Wang et al., "Increased Feeding in Fatty Zucker Rats by the Thiazolidinedione BRL 49653 (Rosiglitazone) and the Possible Involvement of Leptin and Hypothalamic Neuropeptide Y," Br. J. Pharmacol. 122:1405-1410 (1997).

Weiss, R., "Dementia tied to Tiny Strokes," Washington Post, pp. 1 and 12 (Mar. 12, 1997).

Weldon et al., "Fibrillar $\beta$-Amyloid Induces Microglial Phagocytosis, Expression of Inducible Nitric Oxide Synthase, and Loss of a Select Population of Neurons in the Rat CNS in Vivo," J. Neurosci. 18:2161-2173 (1998).

Wickelgren, I., "Tracking Insulin to the Mind," Science 280:517-519 (Apr. 1998).

Wilson, T.M. et al., "The PPARs: From Orphan Receptors to Drug Discovery," J. Med. Chem. 43:527-550 (2000).

Wu, "Endothelial Prostaglandin and Nitric Oxide Synthesis In Atherogenesis and Thrombosis," J. Formos. Med. Assoc. 95:661-666 (1996).

Wu and Wallace, "The Ligation of Amplification Reaction (LAR)—Amplification of Specific DNA Sequences Using Sequential Rounds of Template-Dependent Ligation," Genomics 4:560-569 (1989).

Xu, Yong-Yao et al., "Ethanol inhibits insulin receptor substrate-1 tyrosine phosphorylation and insulin-stimulated neuronal thread protein gene expression," *Biochemical Journal*, 310(1):125-132, 1995.

Yamamoto et al., "Transcriptional Roles of Nuclear Factor KB and Nuclear Factor-Interleukin-6 in the Tumor Necrosis Factor $\alpha$-Dependent Induction of Cyclooxygenase-2 in MC3T3-E1 Cells," J. Biol. Chem. 270:31315-31320 (1995).

Yanagisawa, M. et al., "Starvation induces tau hyperphosphorylation in mouse brain: implications for Alzheimer's disease." FEBS Lett. 461:329-33 (1999).

Zenobi, Peter et al., "Effects of Insulin-like Growth Factor-I on Glucose Tolerance, Insulin Levels, and Insulin Secretion," *Journal of Clin. Invest.*, 89:1908-1913, 1992.

Zhang et al., "Experimental Analysis of Progressive Necrosis after Spinal Cord Trauma in the Rat: Etiological Role of the Inflammatory Response," Exp. Neuro. 143:141-152 (1997).

Zhu et al., "Cytokine Production and the Pathogenesis of Experimental Autoimmune Neuritis and Guillain-Barré Syndrome," J. Neuroimmunol. 84:40-52 (1998).

International Search Report for PCT/US 99/30066, International Publication No. WO 00/35437, dated Aug. 23, 2000.

Arbeeny, C.M., "Novel Drug Development Strategies for the Treatment of Insulin Resistance," Drug & Market Dev. 9:204-209 (1998).

Compton et al., "Mood, Cognition and Alzheimer's Disease," (abstract) Database SCISEARCH, Best Practice and Research in Clinical Obstetrics & Gynaecology: 16(3): 357-370 (2002).

Gottfries, "Therapy Options in Alzheimers-disease," (abstract) Database SCISEARCH, British Journal of Clinical Practice: 48(6): 327-330 (1994).

Mandelkow et al., "Tau Protein and Alzheimer's Disease," (abstract) Database MEDLINE, Neurobiology of Aging 15(Suppl. 2): S85-86 (1994).

Thomas et al., "Aspirin and non-steroidal anti-inflammatory drugs inhibit amyloid-beta aggregation," (abstract) Database CAPLUS, NeuroReport 12(15): 3263-3267 (2001).

de la Monte et al., "Review of insulin and insulin-like growth factor expression, signaling, and malfunction in the central nervous system: Relevance to Alzheimer's disease," Journal of Alzheimer's Disease, 7: 45-61 (2005).

Steen et al., "Impaired insulin and insulin-like growth factor expression and signaling mechanisms in Alzheimer's disease—is this type 3 diabetes?," Journal of Alzheimer's Disease, 7: 63-80 (2005).

Roses, Allen D., patent application filed on Sep. 22, 2005, at the U.S. Patent and Trademark Office for "Novel Method."

Alessi et al., "The role of PI 3-kinase in insulin action," *Biochim. Biophys. Acta*, 1436:151-164 (1998).

Beal et al., "Somatostatin: alterations in the central nervous system in neurological diseases," *Res. Publ. Assoc. Res. Nerv. Ment. Dis.*, 64: 215-257 (1986).

Bernstein et al., "Insulin-degrading enzyme in the Alzheimer's disease brain: prominent localization in neurons and senile plaques," *Neurosci. Lett.*, 263: 161-164 (1999).

Bertram et al., "Evidence for genetic linkage of Alzheimer's disease to chromosome 10q.," *Science*, 290: 2302-2303 (2000).

Braak et al., "Diagnostic criteria for neuropathologic assessment of Alzheimer's disease," *Neurobiol. Aging*, 18: S85-S88 (1997).

Brunet et al., "Akt promotes cell survival by phosphorylating and inhibiting a Forkhead transcriptin factor," *Cell*, 96: 857-868 (1999).

Bucht et al., "Changes in blood glucose and insulin secretion in patients with senile dementia of Alzheimer type," *Acta Med. Scand.*, 213: 387-392 (1983).

Burgering et al., "Protein kinase B (c-Akt) in phosphatidylinositol-3-OH kinase signal transduction," *Nature*, 376: 599-602 (1995).

Carantoni et al., "Alzheimer disease and vascular dementia: relationships with fasting glucose and insulin levels," *Dement. Geriatr. Cogn. Discard.*, 11: 176-180 (2000).

Carson et al., "Insulin-like growth factor I increases brain growth and central nervous system myelination in transgenic mice." *Neuron*, 10: 729-740 (1993).

Connor et al., "Insulin-like growth factor-I (IGF-I) immunoreactivity in the Alzheimer's disease temporal cortex and hippocampus," *Mol. Brain Res.*, 49: 283-290 (1997).

Craft et al., "Insulin effects on glucose metabolism, memory and plasma amyloid precursor protein in Alzheimer's disease differ according to apolipoprotein-E genotype," *Ann. NY Acad. Sci.*, 903: 222-228 (2000).

Craft et al., "Enhancement of memory in Alzheimer disease with insulin and somatostatin, but not glucose," *Arch Gen. Psychiatry*, 56: 1135-1140 (1999).

Craft et al., "Insulin metabolism in Alzheimer's disease differs according to apolipoprotein E genotype and gender," *Neuroendocrinology*, 70: 146-152 (1999).

Crews et al., "Binding of [$^{125}$I]-insulin-like growth factor-1 (IGF-1) in brains of Alzheimer's and alcoholic patients," *Adv. Exp. Med. Biol.*, 293: 483-492 (1991).

Crews et al., "Insulin-like growth factor I receptor binding in brains of Alzheimer's and alcoholic patients," *J. Neurochem.*, 58: 1205-1210 (1992).

D'Ercole et al., "The role of the insulin-like growth factors in the central nervous system," *Mol. Neurobiol.*, 13: 227-255 (1996).

D'Ercole et al., "Use of transgenic mice for understanding the physiology of insulin-like growth factors," *Horm. Res.*, 45 (Supp.1): 5-7 (1996).

D'Ercole, A., "Expression of insulin-like growth factor-I in transgenic mice," *Ann. NY Acad. Sci.*, 692: 149-160 (1993).

da Silva et al., "Quantitative evaluation of the rRNA in Alzheimer's disease," *Mech. Ageing Dev.*, 120: 57-64 (2000).

Datta et al., "Akt phosphorylation of BAD couples survival signals to the cell-intrinsic death machinery," *Cell*, 91: 231-241 (1997).

De Ferrari et al., "Wnt signaling function in Alzheimer's disease," *Brain Res. Rev.*, 33: 1-12 (2000).

De Keyser et al., "Insulin-like growth factor-I receptor densities in human frontal cortex and white matter during aging, in Alzheimer's disease, and in Huntington's disease," *Neurosci. Lett.*, 172: 93-96 (1994).

de la Monte et al., "Partial rescue of ethanol-induced neuronal apoptosis by growth factor activation of phosphoinositol-3-kinase," *Alcohol. Clin. Exp. Res.*, 24: 716-726 (2000).

de la Monte et al., "Mitochondrial DNA damage as a mechanism of cell loss in Alzheimer's disease," *Lab Invest.*, 80: 1323-1335 (2000).

de la Monte et al., "Oxygen free radical injury is sufficient to cause some Alzheimer-type molecular abnormalities in human CNS neuronal cells," *J. Alzheimer's Dis.*, 2: 261-281 (2000).

de la Torre, J., "Critically attained threshold of cerebral hypoperfusion: the CATCH hypothesis of Alzheimer's pathogenesis," *Neurobiol. Aging*, 21: 331-342 (2000).

Delcommenne et al., "Phosphoinositide-3-OH kinase-dependent regulation of glycogen synthase kinase 3 and protein kinase B/AKT by the integrin-linked kinase," *Proc. Natl. Acad. Sci. USA*, 95: 11211-11216 (1998).

Dentremont et al., "Increased insulin-like growth factor-I (IGF-I) expression during early postnatal development differentially increases neuron number and growth in medullary nuclei of the mouse," *Dev. Brain Res.*, 114: 135-141 (1999).

Dorë et al., "Insulin-like growth factor I protects and rescues hippocampal neurons against β-amyloid- and human amylin-induced toxicity," *Proc. Natl. Acad. Sci., USA*, 94: 4772-4777 (1997).

Doré et al., "Protective and rescuing abilities of IGF-I and some putative free radical scavengers against β-amyloid-inducing toxicity in neurons," *Ann. NY Acad. Sci.*, 890: 356-364 (1999).

Doublier et al., "Impaired brain development and hydrocephalus in a line of transgenic mice with liver-specific expression of human insulin-like growth factor binding protein-1," *Growth Horm. IGF Res.*, 10: 267-274 (2000).

Dudek et al., "Regulation of neuronal survival by the serine-threonine protein kinase Akt," *Science*, 275: 661-665 (1997).

Etiene et al., "Cerebrovascular pathology contributes to the heterogeneity of Alzheimer's disease," *J. Alzheimer's Dis.*, 1: 119-134 (1998).

Eves et al., "Akt, a target of phosphatidylinositol 3-kinase, Inhibits apoptosis in a differentiating neuronal cell line," *Mol. Cell Biol.*, 18: 2143-2152 (1998).

Fisman et al., "Metabolic changes in Alzheimer's disease," *J. Am. Geriatr. Soc.*, 36: 298-300 (1988).

Folli et al., "The early intracellular signaling pathway for the insulin/insulin-like growth factor receptor family in the mammalian central nervous system," *Mol. Neurobiol.*, 13: 155-183 (1996).

Frölich et al., "Brain insulin and insulin receptors in aging and sporadic Alzheimer's disease," *J. Neural Transm.*, 105: 423-438 (1998).

Frölich et al., "A disturbance in the neuronal insulin receptor signal transduction in sporadic Alzheimer's disease," *Ann. NY Acad. Sci.*, 893: 290-293 (1999).

Fujisawa et al., "Increased insulin levels after OGTT load in peripheral blood and cerebrospinal fluid of patients with dementia of Alzheimer type," *Biol. Psychiatry*, 30: 1219-1228 (1991).

Garver et al., "Tau phosphorylation in brain slices: pharmacological evidence for convergent effects of protein phosphatases on tau and mitogen-activated protein kinase," *Mol. Pharmacol.*, 47: 745-756 (1995).

Giovannone et al., "Insulin receptor substrate (IRS) transduction system: distinct and overlapping signaling potential," *Diabetes Metab. Res. Rev.*, 16: 434-441 (2000).

Glenner et al., "Alzheimer's disease: initial report of the purification and characterization of a novel cerebrovascular amyloid protein," *Biochem. Biophys. Res. Commun.*, 120: 885-890 (1984).

Halestrap et al., "Mitochondria and cell death," *Biochem. Soc. Trans.*, 28: 170-177 (2000).

Heidenreich et al., "Insulin receptors mediate growth effects in cultured fetal neurons. I. Rapid stimulation of protein synthesis," *Endocrinology*, 125: 1451-1457 (1989).

Hetman et al., "Role of glycogen synthase kinase-3β in neuronal apoptosis induced by trophic withdrawal," *J. Neurosci.*, 20: 2567-2574 (2000).

Hirsch et al., "Mitochondrial permeability transition in apoptosis and necrosis," *Cell Biol. Toxicol.*, 14: 141-145 (1998).

Hong et al., "Insulin and insulin-like growth factor-1 regulate tau phosphorylation in cultured human neurons," *J. Biol. Chem.*, 272: 19547-19553 (1997).

Hoyer et al., "Inhibition of the neuronal insulin receptor: An in vivo model for sporadic Alzheimer disease?," *Ann. NY Acad. Sci.*, 920: 256-258 (2000).

Hoyer et al., "Inhibition of the neuronal insulin receptor causes Alzheimer-like disturbances in oxidative/energy brain metabolism and in behavior in adult rats," *Ann. NY Acad. Sci. USA*, 893: 301-303 (1999).

Hoyer et al., "Predominant abnormality in cerebral glucose utilization in late-onset dementia of the Alzheimer type: a cross-sectional comparison against advanced late-onset and incipient early-onset cases," *J. Neural Transm. [P-DSect]*, 3: 1-14 (1991).

Hoyer et al., "Cerebral excess release of neurotransmitter amino acids subsequent to reduced cerebral glucose metabolism in early-onset dementia of Alzheimer type," *J. Neural Transm.*, 75: 227-232 (1989).

Hoyer et al., "Desensitization of brain insulin receptor: Effect on glucose/energy and related metabolism," *J. Neural Transm.*, Supp 44: 259-268 (1994).

Hoyer, S., "Somatostatin and Alzheimer's disease," *J. Neurol.*, 234: 266-267 (1987).

Hoyer, S., "Brain glucose and energy metabolism abnormalities in sporadic Alzheimer disease. Causes and consequences: an update," *Exp. Gerontol.*, 35: 1363-1372 (2000).

Hoyer, S., "Age as risk factor for sporadic dementia of the Alzheimer type?," *Ann. NY Acad. Sci.*, 719: 248-256 (1994).

Hoyer, S., "Neurodegeneration, Alzheimer's disease, and beta-amyloid toxicity," *Life Sci.*, 55: 1977-1983 (1994).

Jafferali et al., "Insulin-like growth factor-I and its receptor in the frontal cortex, hippocampus, and cerebellum of normal human and alzheimer disease brains," *Synapse*, 38: 450-459 (2000).

Kennedy et al., "Akt/protein kinase B inhibits cell death by preventing the release of cytochrome c from mitochondria," *Mol. Cell. Biol.*, 19: 5800-5810 (1999).

Kulik et al., "Antiapoptotic signaling by the insulin-like growth factor I receptor, phosphatidylinositol 3-kinase, and Akt," *Mol. Cell. Biol.*, 17: 1595-1606 (1997).

Lam et al., "The phosphatidylinositol 3-kinase serine kinase phosphorylates IRS-1. Stimulation by insulin and inhibition by Wortmannin," *J. Biol. Chem.*, 269: 20648-20652 (1994).

Lannert et al., "Intracerebroventricular administration of streptozotocin causes long-term diminutions in learning and memory abilities and in cerebral energy metabolism in adult rats," *Behav. Neurosci.*, 112: 1199-1208 (1998).

Lorenzo et al., "Amyloid fibril toxicity in Alzheimer's disease and diabetes," *Ann. NY Acad. Sci.*, 777: 89-95 (1996).

Lovestone et al., "Alzheimer's disease-like phosphorylation of the microtubule-associated protein tau by glycogen synthase kinase-3 in transfected mammalian cells," *Curr. Biol.*, 4: 1077-1086 (1994).

Mauvais-Jarvis et al., "Understanding the pathogenesis and treatment of insulin resistance and type 2 diabetes mellitus: what can we learn from transgenic and knockout mice?," *Diabetes Metab.*, 26: 433-448 (2000).

McDermott et al., "Degradation of Alzheimer's β-amyloid protein by human and rat brain peptidases: involvement of insulin-degrading enzyme," *Neurochem Res.*, 22: 49-56 (1997).

Meneilly et al., "Alterations in glucose metabolism in patients with Alzheimer's disease," *J. Am. Geriatr. Soc.*, 41: 710-714 (1993).

Messier et al., "Glucose regulation and cognitive functions: relation to Alzheimer's disease and diabetes," *Behav. Brain Res.*, 75: 1-11 (1996).

Mill et al., "Insulin, Insulin-like growth factor II, and nerve growth factor effects on tubulin mRNA levels and neurite formation," *Proc. Natl. Acad. Sci. USA*, 82: 7126-7130 (1985).

Moroo et al., "Loss of insulin receptor immunoreactivity from the substantia nigra pars compacta neurons in Parkinson's disease," *Acta Neuropathol.*, 87: 343-348 (1994).

Mustafa et al., "Decreased plasma insulin-like growth factor-I level in familial Alzheimer's disease patients carrying the Swedish APP 670/671 mutation," *Dement. Geriatr. Cogn. Disord.*, 10: 446-451 (1999).

Myers et al., "The IRS-1 signaling system," *Trends Biochem. Sci.*, 19: 289-293 (1994).

Nagy et al., "Assessment of the pathological stages of Alzheimer's disease in thin paraffin sections: a comparative study," *Dement. Geriatr. Cogn. Disord.*, 9: 140-144 (1998).

Ni et al., "Impaired brain development and reduced astrocyte response to injury in transgenic mice expressing IGF binding protein-1," *Brain Res.*, 769: 97-107 (1997).

Nillni et al., "Identification of the thyrotropin-releasing hormone precursor, its processing products, and its coexpression with convertase 1 in primary cultures of hypothalamic neurons: anatomic distribution of PC1 and PC2," *Endocrinology*, 137: 5651-5661 (1996).

Nishimura et al., "Presenilin mutations associated with Alzheimer disease cause defective intracellular trafficking of β-catenin, a component of the presenilin protein complex," *Nat. Med.*, 5: 164-169 (1999).

Nishiyama et al., "Expression of the gene encoding the tyrosine kinase-deficient human insulin receptor in transgenic mice," *Gene*, 141: 187-192 (1994).

O'Hare et al., "Intrinsic kinase activity of the insulin receptor," *Int. J. Biochem.*, 22: 315-324 (1990).

O'Kusky et al., "Insulin-like growth factor-I promotes neurogenesis and synaptogenesis in the hippocampal dentate gyrus during post-natal development," *J. Neurosci.*, 20: 8435-8442 (2000).

Ott et al., "Association of diabetes mellitus and dementia: the Rotterdam Study," *Diabetologia*, 39: 1392-1397 (1996).

Ott et al., "Diabetes mellitus and the risk of dementia: The Rotterdam Study," *Neurology*, 53: 1937-1942 (1999).

Pap et al., "Role of glycogen synthase kinase-3 in the phosphatidylinositol 3-kinase/Akt cell survival pathway," *J. Biol. Chem.*, 273: 19929-19932 (1998).

Pastorino et al., "The overexpression of Bax produces cell death upon induction of the mitochondrial permeability transition," *J. Biol. Chem.*, 273: 7770-7775 (1998).

Patrick et al., "Conversion of p35 to p25 deregulates Cdk5 activity and promotes neurodegeneration," *Nature*, 402, 615-622 (1999).

Payão et al., "Ribosomal RNA in Alzheimer's disease and ageing," *Mech. Ageing Dev.*, 105: 265-272 (1998).

Pei et al., "Accumulation of cyclin-dependent kinase 5 (cdk5) in neurons with early stages of Alzheimer's disease neurofibrillary degeneration," *Brain Res.*, 797: 267-277 (1998).

Pérez et al., "Degradation of soluble amyloid β-peptides 1-40, 1-42, and the Dutch variant 1-40Q by insulin degrading enzyme from Alzheimer disease and control brains," *Neurochem. Res.*, 25: 247-255 (2000).

Pete et al., "Postnatal growth responses to insulin-like growth factor i in insulin receptor substrate-1-deficient mice," *Endocrinology*, 140: 5478-5487 (1999).

Plaschke et al. "Action of the diabetogenic drug streptozotocin on glycolytic and glycogenolytic metabolism in adult rat brain cortex and hippocampus," *Int. J. Dev. Neurosci.*, 11: 477-483 (1993).

Puro et al., "Insulin-mediated regulation of neuronal maturation," *Science*, 225: 1170-1172 (1984).

Qiu et al., "Insulin-degrading enzyme regulates extracellular levels of amyloid β-protein by degradation," *J. Biol. Chem.*, 273: 32730-32738 (1998).

Reubi et al., "Somatostatin and Alzheimer's disease: a hypothesis," *J. Neurol.*, 233: 370-372 (1986).

Shpakov et al., "Structural and functional characterization of insulin receptor substrate proteins and the molecular mechanisms of their interaction with insulin superfamily tyrosine kinase receptors and effector proteins," *Membr. Cell Biol.*, 13: 455-484 (2000).

Smith et al., "Insulin signaling and action in fat cells: associations with insulin resistance and type 2 diabetes," *Ann. NY Acad. Sci.*, 892: 119-126 (1999).

Spindler et al., "Nutritional status of patients with Alzheimer's disease: a 1-year study," *J. Am. Diet Assoc.*, 96: 1013-1018 (1996).

Sun et al., "Structure of the insulin receptor substrate IRS-1 defines a unique signal transduction protein," *Nature*, 352: 73-77 (1991).

Sun et al., "Pleiotropic insulin signals are engaged by multisite phosphorylation of IRS-1," *Mol. Cell. Biol.*, 13: 7418-7428 (1993).

Tham et al., "Insulin-like growth factors and somatomedin B in the cerebrospinal fluid of patients with dementia of the Alzheimer type," *Acta Psychiatr. Scand.*, 77: 719-723 (1988).

Tham et al., "Insulin-like growth factors and insulin-like growth factor binding proteins in cerebrospinal fluid and serum of patients with dementia of the Alzheimer type," *J. Neural Transm. [P-DSect. ]*, 5: 165-176 (1993).

Ullrich et al., "Human insulin receptor and its relationship to the tyrosine kinase family of oncogenes," *Nature*, 313: 756-761 (1985).

Unger et al., "Insulin receptors in the central nervous system: localization, signalling mechanisms and functional aspects," *Prog. Neurobiol.*, 36: 343-362 (1991).

Unger et al., "Immunohistochemical localization of insulin receptors and phosphotyrosine in the brainstem of the adult rat," *Neuroscience*, 42: 853-861 (1991).

van Weeren et al., "Essential role for protein kinase B (PKB) in insulin-induced glycogen synthase kinase 3 inactivation. Characterization and dominant-negative mutant of PKB," *J. Biol. Chem.*, 273: 13150-13156 (1998).

Vekrellis et al., "Neurons regulate extracellular levels of amyloid β-protein via proteolysis by insulin-degrading enzyme," *J. Neurosci.*, 20: 1657-1665 (2000).

Virkamäki et al., "Protein-protein interaction in insulin signaling and the molecular mechanisms of insulin resistance," *J. Clin. Invest.*, 103: 931-943 (1999).

White et al., "Insulin rapidly stimulates tyrosine phosphorylation of a $M_r$ 185,000 protein in intact cells," *Nature*, 318: 183-186 (1985).

Wozniak et al., "The cellular and physiological actions of insulin in the central nervous system," *Neurochem. Int.*, 22: 1-10 (1993).

Ye et al., "In vivo actions of insulin-like growth factor-I (IGF-I) on cerebellum development in transgenic mice: evidence that IGF-I increases proliferation of granule cell progenitors," *Dev. Brain Res.*, 95: 44-54 (1996).

Ye et al., "Regulation of insulin-like growth factor I (IGF-I) gene expression in brain of transgenic mice expressing an IGF-I-luciferase fusion gene," *Endocrinology*, 138: 5466-5475 (1997).

Zheng et al., "Insulin-like growth factor-1 (IGF-1): a neuroprotective trophic factor acting via the Akt kinase pathway," *J. Neural Transm. Suppl.* 261-272 (2000).

Broe et al., "A case-control study of Alzheimer's disease in Australia," *Neurology* 40: 1698-1707 (1990).

Cantello et al., "The synthesis of BRL 49853—a novel and potent antihyperglycaemic agent," *Bioorg. Med. Chem. Lett.*, 4:1181-1184 (1994).

Curb et al., "The relationship of diabetes and glucose tolerance to Alzheimer's disease and vascular dementia," *Neurobiol. Aging*, 17(4S): S122 [Abstract 488] (1996).

de la Monte et al., "Modulation of neuronal thread protein expression with neuritic sprouting: relevance to Alzheimer's disease," *Journal of the Nourological Sciances*, 138: 26-35 (1996).

de la Monte et al., "Profiles of neuronal thread protein expression in Alzheimer's disease," *Journal of Neuropathology and Experimental Neurology*, 55: 1038-1050 (1996).

de la Monte et al., "Characterization of the AD7C-NTP cDNA expression in Alzheimer's disease and measurement of a 41-kD protein in cerebrospinal fluid," *J. Clin. Invest.*, 100: 3093-3104 (1997).

da la Monte et al., "Neuronal thread protein gene modulation with cerebral infarction," *Journal of Cerebral Blood Flow & Metabolism*, 17:623-635 (1997).

Ferini-Strambi et al., "Clinical and epidemiological aspects of Alzheimer's disease with presenile onset, a case-control study," *Neuroepidemiology*, 9: 39-49 (1990).

Finch et al., "Aging, metabolism, and Alzheimer disease: Review and hypotheses," *Experimental Neurology*, 143: 82-102 (1997).

Heyman et al., "Alzheimer's disease: A study of epidemiological aspects," *Ann. Neurol.*, 15: 335-341 (1984).

Kokmen et al., "Clinical risk factors for Alzheimer's disease: a population-based case-control study," *Neurology*, 41:1393-1397 (1991).

Landin et al., "Low blood pressure and blood glucose levels in Alzheimer's disease evidence for a hypometabolic disorder?" *J. Intern. Med.*, 233: 357-363 (1993).

Leibson et al., "Risk of dementia among persons with diabetes mellitus: a population-based cohort study," *Am. J, Epidemiol.*, 145:301-308 (1997).

Mortel et al., "Analysis of familial and individual risk factors among patients with ischemic vascular dementia and Alzheimer's disease," *Angiology*, 44: 599-605 (1993).

Nielson et al., "Apolriprotein-E genotyping of diabetic dementia patients: Is diabetes rare in Alzheimer's disease," *J. Am. Geriatr. Soc.*, 44: 897-904 (1996).

Thorpe et al., "Comorbidity of the other chronic age-dependent diseases in dementia," *Aging Clin. Exp. Res.*, 6: 159-166 (1994).

Winograd et al., "Blood glucose and insulin response in patients with senile dementia of the Alzheimer's type," *Biol. Psychiatry*, 30: 507-511 (1991).

Wolf-Klein et al., "Are Alzheimer patients healthier?" *J. Am. Geriatr. Soc.*, 36: 219-224 (1988).

\* cited by examiner

METHOD FOR TREATING OR PREVENTING ALZHEIMER'S DISEASE

CROSS REFERENCE TO RELATED APPLICATIONS

The present application is a continuation of U.S. patent application Ser. No. 09/394,712, filed Sep. 13, 1999, which is a continuation of PCT/US98/04731 filed Mar. 12, 1998. The present application also claims the benefit of U.S. provisional application 60/039,607 filed Mar. 12, 1997. The contents of all of these applications are fully incorporated by reference herein.

BACKGROUND OF THE INVENTION

1. Field of the Invention

The present invention is in the field of medicinal chemistry. In particular, the present invention is related to a sunrising new method to treat or prevent Alzheimer's disease by dietary restriction of carbohydrates and/or administration of an agent which causes reduction in serum insulin levels.

2. Related Art

According to a recent review by Mairin B. Brennan published in *Chemical and Engineering News* 75(3):29-35 (1997), roughly 4 million people in the United States have Alzheimer's disease. Inherited or not, the disease manifests itself with progressively impaired memory leading to mental confusion as the disease systematically kills off nerve cells in the brain. (Brennan.)

The devastating consequences of Alzheimer's disease has led to a prodigious effort to identify drugs that might be useful for treating the condition. Two drugs are currently available for treating Alzheimer's symptoms. Cognex (tarcine), sold by Parke-Davis and CoCensys Inc. was approved by the FDA in 1993. Aricept, sold by Eisai of Japan, was approved late in 1996. Both drugs are designed to improve memory and cognition in the earlier stages of the disease. (Brennan.)

Alzheimer's disease is characterized by amyloid plaque that deposits around and between nerve cells in the brains. The plaques contain fibrillar aggregates of a small peptide called amyloid β-peptide. These plaques are centers for the degeneration of nerve endings. Whether the fibers themselves are themselves toxic is somewhat controversial, in view of transgenic animals which have been engineered to express amyloid β-peptide. These mice make amyloid deposits, and there is damage to nerve cells around the plaque, however, no further neuronal loss is seen in these mice. Thus, there appear to be other mechanisms involved. (Brennan.)

Whether the amyloid plaques are the cause or the consequence of the disease is a perplexing question according to Brennan. However, "all genetic routes to Alzheimer's known today, 'act by increasing production or deposition of amyloid—or both,'" quoting Dennis J. Selkoe, professor of neurology and neuroscience at Harvard Medical School. Laedtke, et al., *Clinical Research* 42(1):65A (1994), have also noted an epidemiological correlation between the deposition of amyloid in islet cells, leading to glucose intolerance and non-insulin-dependent diabetes mellitus, and amyloid β-protein deposition in brain cells, as associated with Alzheimer's disease. The authors conclude that there may be an overlap in the molecular defects that predispose to islet and brain amyloid, and therefore NIDDM and AD.

There is evidence of the over-expression of a protein called neural tread protein (NTP) in Alzheimer's disease neurons (see WO94/23756). This protein has been cloned (referred to as AD10-7), and expressed in cell-free culture.

The cathepsins are a family of enzymes that are usually located in lysosomes. It has been found that the inhibition of cathepsin D using an aspartyl protease inhibitor reduces the formation of β-amyloid protein and the resultant senile plaques. Thus inhibitors of cathepsin D, such as rhodanine derivatives, have been proposed as therapeutic agents for the treatment of Alzheimer's disease. See U.S. Pat. Nos. 5,716,975 and 5,523,314.

A number of companies are seeking new therapeutic agents which cross the blood-brain barrier and inhibit amyloid deposition. One such company is Athena Neurosciences, South San Francisco, who has engineered a transgenic mouse model for the disease. Athena is sorting through hundreds of molecules in a series to look for the best pharmaceutical to take into development. (Brennan.)

One drug candidate developed by Neo-Therapeutics, Irvine, Calif., is nearing clinical trials. The hypoxanthine analog (AIT-082) promotes nerve regeneration in the areas of the brain associated with memory. When the drug is administered directly to the brains of 13 month old mice, about 50% of the animals show a delay of about two months in any memory deficit and the other 50% never develop a memory deficit. This drug activates genes that express growth factor proteins known to reverse memory deficits in aged rodents when directly delivered to the brain. (Brennan.)

Another memory enhancing drug ready for clinical trials is CX516, codeveloped by Gary S. Lynch, a professor of psychobiology at the University of California, Irvine, and Gary A. Rogers, vice president of pharmaceutical discovery at Cirtex Pharmaceuticals, Irvine, Calif. CX516 is an agonist of the AMPA receptor, and promotes the uptake of $Ca^{2+}$ into nerve cells when the brain levels of glutamate are low, as they are in Alzheimer's disease. This drug reversed age-associated memory impairment in rats. (Brennan.)

An over the counter agent that may lessen the symptoms or delay the progression of the disease is the nicotine patch. According to Ken Kellar, a professor of pharmacology at the Georgetown University Medical School, Washington, D.C., epidemiological data indicate that there is a lower incidence of Alzheimer's disease among people who smoke. The nicotine patch is now being tested in 12 month clinical study. (Brennan.)

Estrogen is also being evaluated as an agent that might be helpful in protecting women from Alzheimer's disease. Preliminary results indicate that women who receive estrogen replacement therapy have a lower risk of developing the disease. (Brennan.)

Another agent being evaluated is prednisone. This drug is being tested to see if it can benefit Alzheimer's patients by reducing inflammation in their brains. A further study has just been completed which examined the antioxidant effect of vitamin E and selegiline, a drug used to treat Parkinson's disease. (Brennan.)

In completely unrelated studies, it has been reported that elevated levels of insulin in the body are responsible for many cases of obesity, diabetes, heart disease, high blood pressure, and high cholesterol levels. Michael R. Eades and Mary Dan Eades, "Protein Power," Bantam Books, New York, N.Y. (1996). Patients with any of these conditions have been successfully treated with a dietetic regimen which is designed to reduce insulin levels, primarily by strict limitation of metabolizable carbohydrate in the diet. A further strategy is to ameliorate insulin insensitivity which progresses in severity in middle age, by adding chromium to the diet. By reducing insulin insensitivity, lower levels of insulin are required by the body to clear glucose from the blood.

SUMMARY OF THE INVENTION

The present invention is related to the discovery that high levels of circulating insulin are a root cause of Alzheimer's disease. In particular, it has been discovered that insulin stimulates the increased expression of NTP in nerve cell culture. Since insulin crosses the blood-brain barrier, it is now clear that high levels of insulin stimulate brain nerve cells to secrete NTP and develop the hallmarks of Alzheimer's disease.

The present invention is directed to the treatment or prevention of Alzheimer's disease, in a human, comprising administering to an animal in need thereof an effective amount of an agent which results in lowered serum insulin levels. The agent useful in the present invention is one that is also useful for treating impaired glucose tolerance.

The present invention is also directed to the treatment or prevention of Alzheimer's disease, in a human, comprising restricting the metabolizable carbohydrates in the diet of the human to a level which results in lowered serum insulin levels.

The present invention also relates to a method of improving mentation of a patient with Alzheimer's disease, comprising administering to said patient an effective amount of an agent which increases the insulin sensitivity of the patient.

The present invention also relates to a method of treating or preventing Alzheimer's disease, in a human, comprising administering to an animal in need thereof an effective amount of an agent which results in lowered serum insulin levels and an agent which inhibits the formation of small strokes.

DETAILED DESCRIPTION OF THE PREFERRED EMBODIMENTS

Animals with insulin insensitivity require higher levels of serum insulin to stimulate the metabolism of serum glucose and storage for later use. Although insulin has countless other actions in the body, the main function of insulin is to prevent serum glucose levels from rising too high. Thus, when glucose levels rise, insulin levels rise. However, when cells become resistant to insulin, the insulin receptors begin to malfunction. This malfunction appears to be a result of inherited tendencies and lifestyle abuse (over-consumption of carbohydrates). Thus, the receptors require higher levels of insulin to allow the glucose to be removed from the blood. While low levels of insulin are necessary to clear serum glucose when the insulin receptors are working optimally, insulin insensitive receptors require an excess level of insulin to keep serum glucose within the normal range.

Insulin insensitivity can be diagnosed by determining whether the animal has an elevated insulin level. In the case of humans, insulin levels of over 10 mU/ml indicate that the person has at least some insulin insensitivity. Eades and Eades, supra. Insulin values of 25-50 or more are very high and indicative of a high level of insulin resistance. People with insulin levels above 10 mU/ml are considered to be in need of treatment to reduce insulin levels and thereby treat, prevent or reduce the possibility of having Alzheimer's disease in the future.

Agents which may be administered to animals which lower serum insulin levels include drugs which are known to be useful for treating insulin insensitivity. One example of such an agent is chromium. The insulin receptor requires chromium to function properly. Deficiency of chromium is rampant in the American population as a diet high in starch and sugar puts a heavy demand on the insulin system to handle the incoming carbohydrates. Thus, 100-300 micrograms per day of chromium supplements may be administered, e.g. orally or systemically. Preferably, the dose is 200 micrograms of chromium per day. Preferably, the chromium is administered in the form of a chelate. A preferred chromium chelate is niacin bound chromium.

Another agent which can be used is human insulin-like growth factor I (hIGF-I). Recombinant hIGF-I has been reported to be useful for reducing hyperglycemia in patients with extreme insulin resistance. Schoenle et al. *Diabetologia* 34:675-679(1991). See also Usala et al., *N. Engl. J. Med.* 327:853-857 (1992); and Zenobi et al., *J. Clin. Invest.* 89:1908-1913 (1992). Thus, hIGF-I may be administered by intraperitoneal means to a human in need thereof to treat or prevent the onset of Alzheimer's disease. hIGF-I may be administered, e.g. systemically by injection, to the patient in need thereof in an amount effective which can be determined with no more than routine experimentation.

Other agents which can be used in the practice of the invention include dopamine agonists which have been reported to be useful for treating insulin resistance. See U.S. Pat. No. 5,468,755. An example of a dopamine agonist that can be used is bromocriptine. Other dopamine agonists are described in U.S. Pat. Nos. 5,597,832, 5,602,120 and 5,602,121. Thus, a dopamine agonist may be administered to a human in need thereof to treat or prevent the onset of Alzheimer's disease. Routes of administration for such dopamine agonists are described in U.S. Pat. Nos. 5,468,755, 5,597,832, 5,602,120 and 5,602,121. The dopamine agonist may be administered to the patient in need thereof in an amount effective which is, in general, the amount required for the dopamine agonist to treat insulin resistance according to U.S. Pat. No. 5,468,755.

Other agents which can be used in the practice of the invention include pyruvate and pyruvate precursors which have been reported to improve insulin resistence and lower fasting insulin levels. See U.S. Pat. Nos. 5,472,980 and 5,283,260.

Other agents which can be used in the practice of the invention include thiazolidinediones and related antihyperglycemic agents which have been reported to be useful for treating impaired glucose tolerance in order to prevent or delay the onset of non-insulin-dependent diabetes mellitus. See U.S. Pat. No. 5,478,852. An example of a thiazolidinedione that can be used is troglitazone (brand name Rezulin™) that has recently been approved by the U.S. Food and Drug Administration for treating insulin resistance. Routes of administration for such thiazolidinediones and related antihyperglycemic agents are described in U.S. Pat. No. 5,478,852. The thiazolidinediones and related antihyperglycemic agents may be administered to the patient in an amount effective which is, in general, the amount effect to treat impaired glucose tolerance according to U.S. Pat. No. 5,478,852. See also, U.S. Pat. No. 5,457,109. Unlike sulfonylureas, troglitazone is not an insulin secretagogue, "Physicians' Desk Reference," Medical Economics Company, Montvale, N.J., 2118-2119 (1998).

Additional antihyperglycemic agents include, inter alia, rhodanine derivatives such as the 5-methylene-2-thioxo-4-thiazolidinones, see U.S. Pat. No. 5,716,975; C-substituted pentacycloazoles and N-alkyl-substituted pentacycloazoles, see U.S. Pat. No. 5,641,796; hydroxyurea derivatives, see U.S. Pat. Nos. 5,646,168 and 5,463,070; and piperazinylalkylpyrimidines, see U.S. Pat. No. 4,980,350.

Other agents which can be used in the practice of the invention include benzothiodiazines and related antihypoglycemic agents which have been reported to be useful for treating symptomatic hypoglycemia. These agents function by suppressing insulin levels, thereby causing an increased glucose level in the blood. An example of a benzothiadiazine which can be used is diazoxide (brand name Proglycem™) which is approved by the U.S. Food and Drug Administration for treating hypoglycemia due to hyperinsulinism. See, "Physicians' Desk Reference," Medical Economics Company, Montvale, N.J., 595-597 (1998).

A second method of the invention is directed to the treatment or prevention of Alzheimer's disease by the restriction of metabolizable carbohydrate in the diet. According to the invention, the amount of metabolizable carbohydrate is considered restricted if no more than about 55 grams are ingested per day. Preferably, no more than about 30 grams of metabolizable carbohydrates are ingested. More preferably, no more than about 15 grams of metabolizable carbohydrates are ingested. Most preferably, no more than about 10 grams of metabolizable carbohydrates are ingested. One can easily achieve these lowered levels of carbohydrate ingestion by following the regimens disclosed by Michael R. Eades and Mary Dan Eades in their book entitled "Protein Power," Bantam Books, New York, N.Y. (1996). The regimen disclosed by Michael R. Eades and Mary Dan Eades is designed to reduce serum insulin levels to normal levels and, thereby, treat the symptoms of insulin insensitivity including obesity, diabetes, heart disease, high blood pressure and high cholesterol and triglyceride levels.

Further, one can easily adjust the levels of carbohydrates in the diet by reading nutrition labels on foods. The carbohydrate level on food labels includes the non-metabolizable fiber content. Thus, when determining the metabolizable carbohydrate amount in a serving of the food, the number of grams of fiber must be subtracted. In general, to achieve a diet which is low in metabolizable carbohydrates, one must ingest large amounts of protein from red meat, fowl and fish; vegetables including green leafy vegetables, tomatoes, peppers, avocados, broccoli, egg-plant, zucchini, green beans, asparagus, celery, cucumber, mushrooms and salads. Michael R. Eades and Mary Dan Eades disclose the amounts of metabolizable carbohydrates in a large number of foods which allows one to plan a diet that is very low in metabolizable carbohydrates. See also Robert C. Atkins and Veronica Atkins, "Dr. Atkin's Quick and Easy New Diet Cookbook," Fireside Books, New York, N.Y. (1997).

The present invention also relates to a method of improving mentation of a patient with Alzheimer's disease, comprising administering to said patient an effective amount of an agent which increases the insulin sensitivity of the patient. Several lines of investigation suggest a link between impaired glucose utilization and Alzheimer's disease. This hypothesis has been supported by findings that raising plasma glucose levels through glucose administration in elderly humans and rodents improves memory without affecting motor and nonmemory functions. Craft, S., et al., "Effects of Hyperglycemia on Memory and Hormone Levels in Dementia of the Alzheimer Type: A Longitudinal Study," Behav. Neurosci. 107:926-940 (1993). Thus, according to the present invention, an agent may be administered to a patient with Alzheimer's disease to improve mentation, which agent is effective for treating insulin insensitivity. By decreasing insulin insensitivity, that is by increasing insulin sensitivity, in the patient, glucose utilization is improved in the brain and mentation will improve.

Agents which inhibit the formation of small strokes include aspirin.

The agents described herein may also be administered in conjunction with an antiinflammatory agent such as ibuprofen which has been found useful in some studies in ameliorating Alzheimer's disease.

The agents that have been described herein may also be administered with compounds which modulate ATP production and have thereby been found useful as an alternative energy source to glucose for conditions in which ischemic or hypoxic conditions have compromised ATP production. Such compounds include, inter alia, fructose-1,6-biphosphate, see U.S. Pat. Nos. 4,546,095, 4,703,040, 4,757,052, and 5,039,665; pyruvate, see U.S. Pat. No. 5,395,822; glyceraldehyde-3-phosphate and 3-phosphoglycerate, see U.S. Pat. No. 5,707,971. Administration of these agents may also be useful as an alternative to insulin treatment by providing an energy source alternative to glucose, and may obviate the general decline of aging by enhancing ATP production according to U.S. Pat. No. 5,707,971.

Having now generally described the invention, the same will be more readily understood through reference to the following Examples which are provided by way of illustration, and are not intended to be limiting of the present invention, unless specified.

EXAMPLES

Example 1

Insulin Stimulates the Expression of AD7c-NTP, a Protein which Causes Neurons to Exhibit Neuronal Sprouting and Apoptosis Insulin is an important mediator of growth and differentiation in CNS neurons. Insulin stimulated differentiation of PNET2 cells was associated with rapid (within 10 minutes) but transient increases in the levels of the 39 kD, 18 kD and 15 kD NTP species, followed by sustained increases in synthesis and steady state levels of all five NTP species. In contrast, the failure of insulin to induce differentiation of PNET1 cells was associated with absent insulin modulation of NTP.

Analysis of the signal transduction pathways demonstrated that the insulin-induced up-regulation of NTP molecules in PNET2 cells was mediated through phosphorylation of the insulin receptor substrate-1 (IRS-1) and the insulin receptor β subunit (IRβs) itself. In PNET1 cells, the lack of insulin responsiveness was associated with impaired insulin-mediated tyrosyl phosphorylation of IRS-1, but normal insulin receptor phosphorylation. Correspondingly, the insulin-stimulated association between PI3 kinase and phosphorylated IRS-1 was also impaired in PNET1 cells. In essence, impaired insulin-mediated tyrosyl phosphorylation of IRS-1 in PNET1 cells halted activation of the insulin signal transduction cascade, and subsequent events leading to modulated gene (NTP) expression. PNET1 cells lacked insulin responsiveness and failed to phosphorylate IRS-1, but insulin receptor levels and tyrosyl phosphorylation (PY) of the β-subunit were intact. PNET2 cells responded to insulin stimulation with phosphorylation of IRS-1, up-regulation of NTP, and neuronal differentiation. The results were confirmed by absent association between PI3 kinase and IRS-1-PY in PNET1 cells after insulin stimulation.

Neuritic sprouting and neuronal differentiation were induced in PNET2 and SH-Sy5y cells by insulin, PMA, or RA stimulation. Insulin-mediated neuritic growth was associated with increased expression of the fetal brain and PNET-dominant forms of NTP (15 kD and 18 kD). In contrast, the PMA- and RA-induced neuritic sprouting modulated expression of the 21 kD and 26 kD NTP species, which are primarily expressed in the mature brain, and accumulated in AD brains. Thus, expression of the immature or fetal forms of NTP are regulated by mechanisms and growth factors distinct from those involved in modulating expression of the 21 kD and 26 kD NTP molecules. Therefore, expression of fetal NTP molecules/genes can be mediated through the IRS-1 cascade, whereas expression of adult brain/AD-associated NTP genes can be regulated mainly through protein kinase C pathways.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. A method for the treatment of Alzheimer's disease, in a human, comprising administering to the human in need thereof an effective amount of an agent, wherein the agent is selected from chromium, human insulin-like growth factor-I and a thiazolidinedione, wherein the agent increases the insulin sensitivity of the human, and restricting the metabolizable carbohydrates in the diet of the human to no more than about 55 grams per day.

2. The method of claim 1, wherein the metabolizable carbohydrates in the diet are limited to no more than about 30 grams per day.

3. The method of claim 1, wherein the metabolizable carbohydrates in the diet are limited to no more than about 15 grams per day.

4. The method of claim 1, wherein the metabolizable carbohydrates in the diet are limited to no more than about 10 grams per day.

5. The method of claim 1, wherein said agent is a thiazolidinedione.

* * * * *